United States Patent [19]

Stach et al.

[11] 4,404,018
[45] Sep. 13, 1983

[54] FURFURYL AMIDES OF PHENOXYPHENOXYALKANOIC ACIDS AND HERBICIDAL USE

[75] Inventors: Leonard J. Stach, Riverside; Takeo Hokama, Chicago, both of Ill.

[73] Assignee: Velsicol Chemical Corporation, Chicago, Ill.

[21] Appl. No.: 391,088

[22] Filed: Jun. 23, 1982

[51] Int. Cl.³ ............... A01N 43/08; C07D 307/16; C07D 307/54
[52] U.S. Cl. ........................................ 71/88; 549/493
[58] Field of Search ............................ 71/88; 549/493

[56] References Cited

FOREIGN PATENT DOCUMENTS 11802 11/1979 European Pat. Off. .

Primary Examiner—Richard Raymond
Attorney, Agent, or Firm—Robert J. Schwarz

[57] ABSTRACT

This invention discloses chemical compounds of the formula

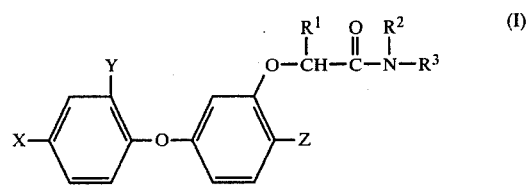

wherein X is halogen or trifluoromethyl; Y is selected from the group consisting of hydrogen, halogen, nitro and cyano; Z is selected from the group consisting of nitro, cyano and halogen; $R^1$ is alkyl; $R^2$ is hydrogen or alkyl; and $R^3$ is furfuryl or tetrahydrofurfuryl. Further discussed are herbicidal compositions utilizing the aforedescribed compounds and methods of controlling undesired vegetation therewith.

10 Claims, No Drawings

FURFURYL AMIDES OF PHENOXYPHENOXYALKANOIC ACIDS AND HERBICIDAL USE

This invention relates to new compositions of matter and more specifically relates to new chemical compounds of the formula:

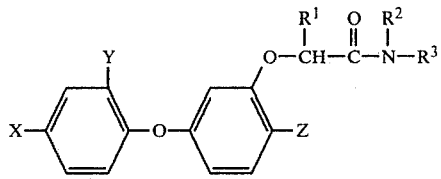

wherein X is halogen or trifluoromethyl; Y is selected from the group consisting of hydrogen, halogen, nitro and cyano; Z is selected from the group consisting of nitro, cyano and halogen; $R^1$ is alkyl; $R^2$ is hydrogen or alkyl; and $R^3$ is furfuryl or tetrahydrofurfuryl.

The compounds of the present invention are unexpectedly useful as selective herbicides.

In a preferred embodiment of the present invention X is chlorine, bromine or trifluoromethyl; Y is hydrogen, chlorine, bromine, nitro or cyano; Z is nitro, cyano, bromine or chlorine; $R^1$ is lower alkyl; $R^2$ is hydrogen or lower alkyl; and $R^3$ is furfuryl or tetrahydrofurfuryl.

In a most preferred embodiment of this invention X is trifluoromethyl and Y is chlorine.

The compounds of the present invention can be prepared by reacting an acid chloride of the formula:

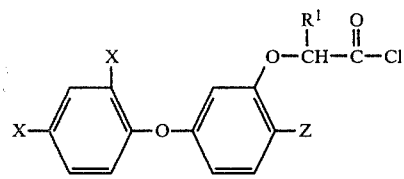

wherein X, Y, Z and $R^1$ are as heretobefore described, with an amine of the formula:

wherein $R^2$ and $R^3$ are as heretobefore described. This reaction can be readily effected by combining the amine of formula III with the acid chloride of formula II in an inert organic solvent such as methylene chloride, in the presence of an acid acceptor such as a tertiary amine. Typically, reaction temperatures below room temperature and those ranging from $-20°$ C. to $0°$ C. are used. After the reaction is completed the reaction mixture is washed with water to remove acid acceptor salt and after drying can be stripped of solvent to yield the desired product. This product can be used as such or further purified by conventional techniques.

The acid chloride of formula II can be prepared from the corresponding free acid by reaction with thionyl chloride. To effect this reaction the acid and thionyl chloride are combined with agitation in an inert, dry organic reaction medium such as toluene. The reaction can be carried out at room temperature or at elevated temperatures such as those ranging up to $90°$ C. After the reaction is completed the desired product can be recovered upon stripping off the solvent used as the reaction medium.

The compounds of formula II and their corresponding free acids are known in the art and are described by Schoenowsky, et. al., in Z. Naturforsch. 35b, 902–908 (1980) as well as in the European Patent Application Nos. 0001641 published June 2, 1979 and 0011802 published June 11, 1980.

Exemplary acid precursors of the compounds of formula II useful in preparing the compounds of the present invention are: 2-[2-nitro-5-(2-chloro-4-trifluoromethylphenoxy)phenoxy]propionic acid, 2-[2-nitro-5-(4-trifluoromethylphenoxy)phenoxy]propionic acid, 2-[2-nitro-5-(2-bromo-4-trifluoromethylphenoxy)phenoxy]-propionic acid, 2-[2-chloro-5-(2-nitro-4-chlorophenoxy)phenoxy]-propionic acid, 2-[2-bromo-5-(2-cyano-4-bromophenoxy)phenoxy]-propionic acid, 2-[2-nitro-5-(2,4-dichlorophenoxy)phenoxy]propionic acid, 2-[2-nitro-5-(2,4-dibromophenoxy)phenoxy]propionic acid, 2-[2-nitro-5-(4-chlorophenoxy)phenoxy]propionic acid, 2-[2-nitro-5-(4-bromophenoxy)phenoxy]propionic acid, 2-[2-nitro-5-(4-iodophenoxy)phenoxy]propionic acid, 2-[2-cyano-5-(4-fluorophenoxy)phenoxy]propionic acid.

Exemplary compounds of formula III useful in preparing the compounds of the present invention are: furfurylamine, N-methyl-N-furfurylamine, N-ethyl-N-furfurylamine, N-propyl-N-furfurylamine, N-butyl-N-furfurylamine, N-pentyl-N-furfurylamine, N-hexyl-N-furfurylamine, tetrahydrofurfurylamine, N-methyl-N-tetrahydrofurfurylamine, N-ethyl-N-tetrahydrofurfurylamine and the like.

The manner in which the compounds of the present invention can be prepared is more specifically illustrated in the following examples.

EXAMPLE 1

Preparation of 2-[2-nitro-5-(2-Chloro-4-trifluoromethylphenoxy)-phenoxy]propionyl Chloride 2-[2-Nitro-5-(2-Chloro-4-trifluoromethylphenoxy)-phenoxy]propionic acid (100 grams) and toluene (40 ml) were charged into a glass reaction vessel equipped with a magnetic stirrer. The mixture was heated on a steam bath until a solution was obtained. The solution was allowed to cool and thionyl chloride (100 ml) was added dropwise with stirring. After the addition was completed the mixture was warmed to $67°$ C. with continued stirring for a period of about $2\frac{1}{2}$ hours. After this time the mixture was stripped of solvent in a rotary evaporator under reduced pressure leaving as the residue 105 grams of the desired product, 2-[2-nitro-5-(2-chloro-4-trifluoromethylphenoxy)phenoxy]propionyl chloride as a burgundy colored viscous oil.

EXAMPLE 2

Preparation of N-Furfuryl-2-[2-nitro-5-(2-chloro-4-trifluoromethylphenoxy)phenoxy]propionamide Furfurylamine (1 gram; 0.01 mole), methylene chloride (50 ml) and triethylamine were charged into a glass reaction vessel equipped with a thermometer, mechanical stirrer and addition funnel. The reaction mixture was cooled to a temperature of $-10°$ C. and 2-[2-nitro-5-(2-chloro-4-trifluoromethylphenoxy)phenoxy]propionyl chloride (4.3 grams; 0.01 mole) dissolved in methylene chloride (50 ml) was added dropwise with stirring and continued cooling. After the addition was completed the reaction mixture was allowed to warm to room temperature with continued stirring over a period of one hour. After this time the reaction mixture was transferred into a separatory funnel and was washed with water (100 ml), with dilute aqueous sodium bicarbonate (100 ml; 5% conc.) and again with water (100 ml). The washed solution was dried by passing it through phase separation paper and was then stripped of solvent leaving a dark red-brown oil. This oil was subjected to chromatography using a 150 cc clay column and hexane/ethyl acetate mixtures with increasing concentrations of ethyl acetate as the eluant. Fractions 9 and 10 were combined and stripped of solvent to yield the desired product N-furfuryl-2-[2-nitro-5-(2-chloro-4-trifluoromethylphenoxy)phenoxy]propionamide as an orange solid melting at 128° to 130° C.

EXAMPLE 3

Preparation of
N-Furfuryl-2-[2-nitro-5-(2-bromo-4-trifluoromethylphenoxy)-6-nitrophenoxy]propionamide Furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-bromo-4-trifluoromethylphenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-furfuryl-2-[2-nitro-5-(2-bromo-4-trifluoromethylphenoxy)phenoxy]propionamide.

EXAMPLE 4

Preparation of
N-Methyl-N-furfuryl-2-[2-nitro-5-(2-chloro-4-trifluoromethylphenoxy)phenoxy]propionamide N-Methyl-N-furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-chloro-4-trifluoromethylphenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-methyl-N-furfuryl-2-[2-nitro-5-(2-chloro-4-trifluoromethylphenoxy)phenoxy]propionamide.

EXAMPLE 5

Preparation of
N-Ethyl-N-furfuryl-2-[2-nitro-5-(4-fluorophenoxy)phenoxy]propionamide N-Ethyl-N-furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(4-fluorophenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-ethyl-N-furfuryl-2-[2-nitro-5-(4-fluorophenoxy)phenoxy]propionamide.

EXAMPLE 6

Preparation of
N-propyl-N-furfuryl-2-[2-chloro-5-(2-nitro-4-chlorophenoxy)-6-nitrophenoxy]propionamide N-propyl-N-furfurylamine (0.015 mole), triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-chloro-5-(2-nitro-4-chlorophenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-propyl-N-furfuryl-2-[2-chloro-5-(2-nitro-4-chlorophenoxy)phenoxy]propionamide.

EXAMPLE 7

Preparation of
N-butyl-N-furfuryl-2-[2-bromo-5-(2-cyano-4-bromophenoxy)phenoxy]propionamide N-Butyl-N-furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-bromo-5-(2-cyano-4-bromophenoxy)phenoxy]propionyl chloride (0.01 mole) in methylene chloride (50 ml) is added dropwise with stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-butyl-N-furfuryl-2-[2-bromo-5-(2-cyano-4-bromophenoxy)phenoxy]propionamide.

EXAMPLE 8

Preparation of
N-Furfuryl-2-[2-nitro-5-(2-chloro-4-trifluoromethylphenoxy)phenoxy]butyramide Furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-chloro-4-trifluoromethylphenoxy)phenoxy]butyryl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-furfuryl-2-[2-nitro-5-(2-chloro-4-trifluoromethylphenoxy)phenoxy]butyramide.

EXAMPLE 9

Preparation of
N-Methyl-N-furfuryl-2-[2-nitro-5-(2-chloro-4-trifluoromethylphenoxy)phenoxy]pentanamide N-Methyl-N-furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-chloro-4-trifluoromethylphenoxy)phenoxy]pentanoyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-methyl-N-furfuryl-2-[2-nitro-5-(2-chloro-4-trifluoromethylphenoxy)phenoxy]pentanamide.

EXAMPLE 10

Preparation of
N-Furfuryl-2-[2-cyano-5-(2-chloro-4-trifluoromethylphenoxy)phenoxy]hexanamide Furfurylamine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-cyano-5-(2-chloro-4-trifluoromethylphenoxy)phenoxy]hexanoyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. This residue is then purified by subjecting it to elution chromatography using mixtures of ethyl acetate and hexane with increasing concentrations of ethyl acetate as the eluant. The desired fractions determined by IR spectroscopy are then stripped of solvent to yield the desired product N-furfuryl-2-[2-cyano-5-(2-chloro-4-trifluoromethylphenoxy)phenoxy]hexanamide.

EXAMPLE 11

Preparation of
N-Tetrahydrofurfuryl-2-[2-nitro-5-(2-chloro-4-trifluoromethylphenoxy)phenoxy]propionamide Tetrahydrofurfurylamine (1.5 grams; 0.015 mole), methylene chloride (50 ml) and triethylamine (5 ml) were charged into a glass reaction vessel equipped with a stirrer, thermometer and addition funnel. The reaction mixture was cooled to −10° C. and 2-[2-nitro-5-(2-chloro-4-trifluoromethylphenoxy)phenoxy]propionyl chloride (4.3 grams) dissolved in methylene chloride (50 ml) was added dropwise with stirring. After the addition was completed stirring was continued for a period of about one hour. After this time the reaction mixture was transferred into a separatory funnel and was washed with water (300 ml) and with dilute aqueous sodium bicarbonate (100 ml). The washed solution was then dried by passing it through phase separation paper and was stripped of solvent in a rotary evaporator under aspirator pressure leaving a dark brown-orange oil as the residue. The residue was then dissolved in toluene (6 ml) and charged onto 150 cc of clay for chromatography. The product was then eluted using ethyl acetate-hexane mixtures with increasing concentrations of ethyl acetate. Twelve fractions were collected. Fractions 5 and 6 were combined and stripped of solvents to yield the desired product N-tetrahydrofurfuryl-2-[2-nitro-5-(2-chloro-4-trifluoromethylphenoxy)phenoxy]propionamide as an orange solid melting at 102° to 104° C.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 12

Preparation of a Dust

| Product of Example 2 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compound of the present invention are also useful when combined with other herbicides and/or defoliants, dessicants, growth inhibitors and the like in the herbicidal compositions theretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4-(2,4-DB), 2,4-DEB, 4-CPB, 4-CPP, 2,4,5-TB, 2,4,5-TES, 3,4-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)-morpholine, 1-(chloracetyl) piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocyil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrod, matricaria, wild barley, campion, chamomile, burdock, mullein, roundleaved mallow, bull thistle, hounds-tongue, moth mullein, and purple star thistle; or perennials such as white cockle, perennial ryegrass, quackgrass Johnson grass, Canada thistle, hedge binweed, Bermuda grass, sheep sorrel, curly dock, nutgrass, field chickweed, dandelion, campanula, field bindweed, Russion knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following data set out in Table I. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 10 to 15 days after treatment and was rated on the scale of from 0 to 10 heretobefore described. The effectiveness of these compounds is demonstrated by the following data set forth in Table II. Values with decimal places again are the result of averaging of replicate experiments.

TABLE I

Pre-Emergence Screen 14 & 21-Day Tests

| Compound | #/Acre | WMSD 14 | WMSD 21 | BDWD 14 | BDWD 21 | PIGW 14 | PIGW 21 | JMWD 14 | JMWD 21 | VTLF 14 | VTLF 21 | MNGY 14 | MNGY 21 | YLFX 14 | YLFX 21 | BNGS 14 | BNGS 21 | JNGS 14 | JNGS 21 |
|---|---|---|---|---|---|---|---|---|---|---|---|---|---|---|---|---|---|---|---|
| Product of Example 2 | 4 | NE | NE | — | — | 10 | 10 | NE | NE | NE | NE | 8 | 8 | 10 | 10 | 10 | 10 | 10 | 10 |
| | 1 | 10 | 10 | 7 | 8 | NE | NE | 9 | 10 | NE | NE | 10 | 10 | 7 | 7 | 10 | 10 | 5 | 4 |
| | .5 | 9 | 10 | 3 | 3 | 9 | 10 | 10 | 10 | 10 | 10 | 6 | 6 | 2 | 0 | 10 | 10 | 3 | 3 |
| | .25 | 6 | 3 | 7 | 6 | 2 | 10 | NE | NE | 9 | 10 | 5 | 3 | 0 | 0 | 7 | 7 | 4 | 3 |
| | .125 | 4 | 3 | 0 | 0 | 4 | 2 | NE | NE | 0 | 0 | 10 | 10 | 0 | 0 | 6 | 6 | 3 | 2 |
| Product of Example 11 | 4 | 10 | 10 | — | — | NE | NE | NE | NE | 10 | 10 | 8 | 9 | 10 | 10 | NE | NE | 10 | 10 |
| | 1 | 10 | 10 | 8 | 9 | 10 | 10 | NE | NE | 9 | 10 | 8 | 9 | 9 | 10 | 10 | 10 | 10 | 10 |
| | .5 | 10 | 10 | 4 | 4 | 10 | 10 | NE | NE | 10 | 10 | 10 | 10 | 10 | 10 | 10 | 10 | 10 | 10 |
| | .25 | 7 | 7 | 0 | 1 | 10 | 10 | NE | NE | 10 | 10 | 4 | 0 | 0 | 0 | 6 | 3 | 3 | 2 |
| | .125 | 6 | 3 | 0 | 0 | 10 | 10 | 2 | 10 | 4 | 3 | 1 | 0 | 4 | 6 | 6 | 3 | 7 | 7 |

| Compound | #/Acre | QKGS 14 | QKGS 21 | WOAT 14 | WOAT 21 | CBGS 14 | CBGS 21 | SPGT 14 | SPGT 21 | CTGS 14 | CTGS 21 | SUBT 14 | SUBT 21 | SOYB 14 | SOYB 21 | COTN 14 | COTN 21 | PTBN 14 | PTBN 21 |
|---|---|---|---|---|---|---|---|---|---|---|---|---|---|---|---|---|---|---|---|
| Product of Example 2 | 4 | — | — | 6 | 7 | NE | NE | — | — | 10 | 8 | — | — | — | — | — | — | — | — |
| | 1 | 7 | 7 | 2 | 0 | 8 | 7 | 10 | 10 | 5 | 2 | 10 | 10 | 6 | 5 | 5 | 4 | 10 | 10 |
| | .5 | 3 | 1 | 1 | 0 | 3 | 7 | 4 | 5 | 1 | 0 | 6 | 4 | 4 | 2 | 0 | 0 | 4 | 6 |
| | .25 | 3 | 0 | 4 | 0 | 4 | 7 | 9 | 10 | 0 | 0 | 10 | 10 | 4 | 2 | 1 | 1 | 10 | 10 |
| | .125 | 0 | 0 | 0 | 0 | 3 | 0 | 4 | 8 | 0 | 0 | 2 | 0 | 4 | 3 | 0 | 0 | 4 | 4 |
| Product | | | | | | | | | | | | | | | | | | | |

TABLE I-continued

Pre-Emergence Screen 14 & 21-Day Tests

| of Example 11 | | | | | | | | | | | | | | | | | | | |
|---|---|---|---|---|---|---|---|---|---|---|---|---|---|---|---|---|---|---|---|
| | 4 | — | — | 7 | 10 | NE | NE | — | — | 10 | 10 | — | — | — | — | — | — | — | — |
| | 1 | 4 | 7 | 10 | 10 | NE | NE | NE | NE | NE | 8 | 10 | 10 | 10 | 10 | 3 | 10 | 10 | 10 |
| | .5 | 0 | 0 | 7 | 6 | NE | NE | NE | NE | NE | NE | 10 | 10 | 4 | 3 | 1 | 2 | 5 | 4 |
| | .25 | 0 | 0 | 0 | 0 | 9 | 9 | NE | NE | 2 | 5 | 10 | 10 | 4 | 0 | 0 | 2 | 6 | 5 |
| | .125 | 0 | 0 | 0 | 0 | 10 | 10 | 7 | 0 | 0 | 0 | 10 | 10 | 0 | 0 | 0 | 0 | 2 | 2 |

| Compound | #/Acre | ALFA 14 | ALFA 21 | WHT 14 | WHT 21 | RICE 14 | RICE 21 | SORG 14 | SORG 21 | CORN 14 | CORN 21 | OAT 14 | OAT 21 | YNSG 14 | YNSG 21 |
|---|---|---|---|---|---|---|---|---|---|---|---|---|---|---|---|
| Product of Example 2 | 4 | — | — | — | — | — | — | — | — | — | — | — | — | NE | NE |
| | 1 | 10 | 10 | 4 | 6 | 1 | 0 | 4 | 4 | 4 | 3 | 1 | 0 | — | — |
| | .5 | 9 | 8 | 2 | 2 | 0 | 0 | 3 | 3 | 5 | 4 | 0 | 0 | — | — |
| | .25 | 8 | 10 | 2 | 1 | 2 | 0 | 2 | 0 | 3 | 2 | 0 | 0 | — | — |
| | .125 | 0 | 0 | 0 | 0 | 1 | 0 | 4 | 3 | 3 | 3 | 0 | 0 | — | — |
| Product of Example 11 | 4 | — | — | — | — | — | — | — | — | — | — | — | — | 3 | 5 |
| | 1 | 10 | 10 | 6 | 4 | 5 | 3 | 6 | 5 | 6 | 6 | 10 | 10 | — | — |
| | .5 | 10 | 10 | 4 | 4 | 0 | 0 | 6 | 7 | 4 | 3 | 10 | 10 | — | — |
| | .25 | 7 | 9 | 0 | 1 | 0 | 0 | 2 | 1 | 2 | 3 | 1 | 0 | — | — |
| | .125 | 7 | 8 | 0 | 0 | 0 | 0 | 1 | 0 | 0 | 0 | 0 | 0 | — | — |

TABLE II

Post-Emergence Screen

| Compound | #/Acre | WMSD | BDWD | PIGW | JMWD | VTLF | MNGY | YLFX | BNGS | JNGS | QKGS | WOAT | CBGS |
|---|---|---|---|---|---|---|---|---|---|---|---|---|---|
| Product of Example 2 | 4 | 10 | 7 | — | 10 | 6 | 10 | — | 10 | 10 | — | 4 | 10 |
| | 1 | 10 | 10 | 10 | 10 | 10 | 10 | 9 | 10 | 10 | 10 | 10 | 10 |
| | .5 | 10 | 10 | 10 | 10 | 10 | 10 | 10 | 7 | 10 | 10 | .6 | 10 |
| | .25 | 10 | 10 | 10 | 10 | 10 | 10 | 4 | 7 | 10 | 10 | 5 | 9 |
| | .125 | 10 | 9* | 10 | 10* | 10* | 10 | 0 | 5 | 10 | 5 | 10 | 9 |
| | .062 | — | 3 | — | 10 | 10 | — | — | — | — | — | — | — |
| | .031 | — | 5 | — | 10 | 10 | — | — | — | — | — | — | — |
| | .015 | — | 1 | — | 10 | 10 | — | — | — | — | — | — | — |
| Product of Example 11 | 4 | 10 | 10 | — | 10 | — | 10 | 10 | 10 | 10 | — | 8 | 10 |
| | 1 | 10 | 10 | 10 | 10 | 10 | 10 | 10 | 10 | 10 | 10 | 10 | 10 |
| | .5 | 10 | 10 | 10 | 10 | 10 | 10 | 10 | 10 | 10 | 9 | 2 | 10 |
| | .25 | 10 | 10 | 10 | 10 | 10 | 10 | 0 | 9 | 10 | 5 | 0 | 9 |
| | .125 | 10 | 8.5* | 10 | 10* | 10* | 9 | 0 | 6 | 8 | 0 | 1 | 1 |
| | .062 | — | 5 | — | 10 | 10 | — | — | — | — | — | — | — |
| | .031 | — | 3 | — | 10 | 10 | — | — | — | — | — | — | — |
| | .015 | — | 0 | — | 10 | 10 | — | — | — | — | — | — | — |

| Compound | #/Acre | SPGT | CTGS | SUBT | COTN | SOYB | PTBN | ALFA | SORG | WHT | RICE | CORN | OAT | YNSG |
|---|---|---|---|---|---|---|---|---|---|---|---|---|---|---|
| Product of Example 2 | 4 | — | — | — | — | 7 | — | — | — | — | — | — | — | 2 |
| | 1 | 10 | 7 | 10 | 10 | 7 | 10 | 10 | 6 | 7 | 8 | 3 | 10 | — |
| | .5 | 10 | 0 | 10 | 10 | 6 | 10 | 10 | 3 | 5 | 3 | 1 | 3 | — |
| | .25 | 10 | 0 | 10 | 10 | 3 | 10 | 10 | 5 | 1 | 1 | 0 | 1 | — |
| | .125 | 9 | 0 | 10 | 3* | — | — | 4 | 0 | 1 | 0 | 1 | — | — |
| | .062 | — | — | — | — | 2 | — | — | — | — | — | — | — | — |
| | .031 | — | — | — | — | 2 | — | — | — | — | — | — | — | — |
| | .015 | — | — | — | — | 1 | — | — | — | — | — | — | — | — |
| Product of Example 11 | 4 | — | — | — | — | 9 | — | — | — | — | — | — | — | 4 |
| | 1 | 10 | 5 | 10 | 10 | 8 | 10 | 10 | 9 | 5 | 5 | 10 | 10 | — |
| | .5 | 10 | 0 | 10 | 10 | 7 | 10 | 10 | 5 | 3 | 0 | 6 | 10 | — |
| | .25 | 10 | 0 | 10 | 10 | 4 | 10 | — | 1 | 0 | 0 | 0 | 10 | — |
| | .125 | 10 | 0 | 8 | 10 | 3.5* | 10 | — | 1 | 0 | 0 | 0 | 8 | — |
| | .062 | — | — | — | — | 3 | — | — | — | — | — | — | — | — |
| | .031 | — | — | — | — | 3 | — | — | — | — | — | — | — | — |
| | .015 | — | — | — | — | 2 | — | — | — | — | — | — | — | — |

| Compound | #/Acre | CKBR | PSDA | RAPE |
|---|---|---|---|---|
| Product of Example 2 | 4 | — | — | — |
| | 1 | — | — | — |
| | .5 | — | — | — |
| | .25 | — | — | — |
| | .125 | 5 | 10 | 10 |
| | .062 | 3 | 10 | 10 |
| | .031 | 5 | 10 | 8 |
| | .015 | 3 | 3 | 7 |
| Product of Example 11 | 4 | — | — | — |
| | 1 | — | — | — |
| | .5 | — | — | — |

TABLE II-continued

Post-Emergence Screen

|  |  |  |  | .25 | — | — | — |
|---|---|---|---|---|---|---|---|
|  |  |  |  | .125 | 7 | 10 | 10 |
|  |  |  |  | .062 | 3 | 10 | 9 |
|  |  |  |  | .031 | 2 | 10 | 7 |
|  |  |  |  | .015 | 0 | 5 | 2 |
| Compound | #/Acre | IVMNGY | CDCK | WMSTD | SKPD | ANNGY |
| Product of Example 2 | .125 | 10 | 10 | 10 | 3 | 6 |
|  | .062 | 10 | 10 | 10 | 2 | 7 |
|  | .031 | 7 | 10 | 10 | 0 | 6 |
|  | .015 | 10 | 2 | 3 | 0 | 10 |
| Product of Example 11 | .125 | 7 | 10 | 10 | 9 | 10 |
|  | .062 | 10 | 3 | 6 | 1 | 6 |
|  | .031 | 10 | 3 | 3 | 1 | 4 |
|  | .015 | 7 | 0 | 3 | 0 | 4 |

*Average of two or more tests

ABBREVIATIONS FOR WEEDS & CROPS
WMSD = Wild Mustard
BDWD = Bindweed
PIGW = Pigweed
JMWD = Jimsonweed
VTLF = Velvetleaf
MNGY = Morningglory
BNGS = Barnyardgrass
JNGS = Johnsongrass
QKGS = Quackgrass
WOAT = Wild Oat
CBGS = Crabgrass
SPGT = Sprangletop
CTGS = Cheatgrass
SUBT = Sugarbeet
YLFX = Yellow Foxtail
SOYB = Soybean
PTBN = Pinto Bean
ALFA = Alfalfa
SORG = Sorgum
WHT = Wheat
YNSG = Yellow Nutsedge
CKBR = Cocklebur
PSDA = Prickley Sida
IVMNGY = Ivyleaf Morningglory
CDCK = Curlydock
WMSTD = Wild Mustard
SKPD = Sicklepod
ANNGY = Annual Morningglory
COTN = Cotton

We claim:

1. A compound of the formula

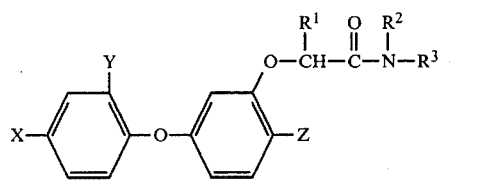

wherein X is halogen or trifluoromethyl; Y is selected from the group consisting of hydrogen, halogen, nitro and cyano; Z is selected from the group consisting of nitro, cyano and halogen; $R^1$ is alkyl; $R^2$ is hydrogen or alkyl; and $R^3$ is furfuryl or tetrahydrofurfuryl.

2. The compound of claim 1, N-furfuryl-2-[3-(2-chloro-4-trifluoromethylphenoxy)-6-nitrophenoxy]propionamide.

3. The compound of claim 1, N-tetrahydrofurfuryl-2-[2-nitro-5-(2-chloro-4-trifluoromethylphenoxy)phenoxy]propionamide.

4. The compound of claim 1, N-furfuryl-2-[2-nitro-5-(2-bromo-4-trifluoromethylphenoxy)phenoxy]propionamide.

5. The compound of claim 1, N-methyl-N-furfuryl-2-[2-nitro-5-(2-chloro-4-trifluoromethylphenoxy)phenoxy]propionamide.

6. The compound of claim 1, N-ethyl-N-furfuryl-2-[2-nitro-5-(4-fluorophenoxy)phenoxy]propionamide.

7. The compound of claim 1, N-propyl-N-furfuryl-2-[2-chloro-5-(2-nitro-4-chlorophenoxy)phenoxy]propionamide.

8. The compound of claim 1, N-butyl-N-furfuryl-2-[2-bromo-5-(2-cyano-4-bromophenoxy)phenoxy]propionamide.

9. A herbicidal composition comprising an inert carrier and as the essential active ingredient, in a quantity toxic to weeds, a compound of claim 1.

10. A method of controlling weeds which comprises contacting said weeds, or the locus of said weeds, with a herbicidal composition of claim 9.

* * * * *